United States Patent
Andersen et al.

(10) Patent No.: US 11,684,308 B2
(45) Date of Patent: Jun. 27, 2023

(54) METHOD AND SYSTEM FOR MEASURING THE LAXITY OF A JOINT OF A HUMAN OR AN ANIMAL

(71) Applicant: Aalborg Universitet, Aalborg (DK)

(72) Inventors: Michael Skipper Andersen, Nørresundby (DK); Jonas Stensgaard Stoltze, Aalborg (DK); Dennis Pedersen, Aalborg (DK)

(73) Assignee: Aalborg Universitet, Aalborg Øst (DK)

( * ) Notice: Subject to any disclaimer, the term of this patent is extended or adjusted under 35 U.S.C. 154(b) by 784 days.

(21) Appl. No.: 16/476,647

(22) PCT Filed: Jan. 8, 2018

(86) PCT No.: PCT/DK2018/050003
§ 371 (c)(1),
(2) Date: Jul. 9, 2019

(87) PCT Pub. No.: WO2018/130256
PCT Pub. Date: Jul. 19, 2018

(65) Prior Publication Data
US 2020/0000399 A1  Jan. 2, 2020

(30) Foreign Application Priority Data

Jan. 8, 2018 (DK) .......................... PA 2017 70017

(51) Int. Cl.
*A61B 5/00* (2006.01)
*A61B 5/055* (2006.01)
(Continued)

(52) U.S. Cl.
CPC .......... *A61B 5/4528* (2013.01); *A61B 5/0048* (2013.01); *A61B 5/055* (2013.01);
(Continued)

(58) Field of Classification Search
CPC ..... A61B 5/4528; A61B 5/0048; A61B 5/055; A61B 5/1121; A61B 6/032; A61B 8/5207;
(Continued)

(56) References Cited

U.S. PATENT DOCUMENTS 6,551,258 B1 * 4/2003 Herling ................ A61B 5/4528
600/595
2004/0254771 A1 * 12/2004 Riener .................. G09B 23/32
703/7
(Continued)

FOREIGN PATENT DOCUMENTS

| EP | 2042110 | 4/2009 |
|---|---|---|
| EP | 2309462 | 4/2011 |
| WO | 2010/083301 A2 | 7/2010 |

OTHER PUBLICATIONS

Illes et al., "The EOS™ imaging system and its uses in daily orthopaedic practice," (Feb. 28, 2012) International Orthopaedics (SICOT) 36:1325-1331. (Year: 2012).*
(Continued)

*Primary Examiner* — Joel Lamprecht
*Assistant Examiner* — Ashish S Jasani
(74) *Attorney, Agent, or Firm* — Klarquist Sparkman LLP

(57) ABSTRACT

The invention relates to a method of determining the laxity of a joint (9, 15) of a human (5) or an animal. The method comprises providing at least one patient-specific geometrical model (1) of at least one bone and/or at least one prosthesis comprised by the joint. Known loads are applied to the joint or to a part of the body connected to the joint, and a series of actual images (16) of the joint are obtained while the loads are applied. Then the at least one patient-specific geometrical model (1) is registered onto the actual images (16). Based thereon relative displacement and/or rotation of the at least one bone and/or at least one prosthesis is
(Continued)

calculated as a function of the applied loads, and based thereon a measure of the laxity of the joint is determined. The invention further relates to a system for performing such a method and to a computer readable medium for performing such a method.

16 Claims, 3 Drawing Sheets

(51) Int. Cl.
  *A61B 5/11* (2006.01)
  *A61B 6/03* (2006.01)
  *A61B 8/08* (2006.01)

(52) U.S. Cl.
  CPC ............ *A61B 5/1121* (2013.01); *A61B 6/032* (2013.01); *A61B 8/5207* (2013.01)

(58) Field of Classification Search
  CPC ................ A61B 5/1071; A61B 5/4504; A61B 2034/105; A61B 34/10; A61B 5/103; A61B 5/1075; G16B 5/00; G16H 20/40; G16H 50/50
  See application file for complete search history.

(56) References Cited

U.S. PATENT DOCUMENTS

| | | | | |
|---|---|---|---|---|
| 2007/0219561 | A1* | 9/2007 | Lavallee | A61B 90/36 606/90 |
| 2009/0088674 | A1* | 4/2009 | Caillouette | A61B 5/4528 600/595 |
| 2010/0076563 | A1* | 3/2010 | Otto | A61B 5/4824 623/20.14 |
| 2013/0110250 | A1* | 5/2013 | Li | A61B 34/10 623/20.21 |
| 2014/0081181 | A1* | 3/2014 | Branch | A61B 5/1121 600/595 |
| 2014/0260701 | A1* | 9/2014 | Imhauser | A61B 5/1124 73/865.4 |
| 2016/0278754 | A1* | 9/2016 | Todorov | A61F 2/3859 |
| 2016/0317309 | A1* | 11/2016 | Al Hares | A61F 2/30942 |

OTHER PUBLICATIONS

Forlani et al., "A New Test Rig for In-Vitro Evaluation of the Knee Joint Behaviour," (Apr. 24, 2015), [Dissertation thesis], Alma Mater Studiorum Università di Bologna. Dottorato di ricerca in Meccanica e scienze avanzate dell'ingegneria, 27 Cielo. (Year: 2015).*

Ding, Boyin, "A Study of a Gough-Stewart Platform based Manipulator for Applications in Biomechanical Testing," (Oct. 15, 2013), Thesis for the degree of Ph.D. in Mechanical Engineering, School of Mechanical Engineering The University of Adelaide. (Year: 2013).*

Carpenter et al. "A new device for measuring knee rotational kinematics using magnetic resonance imaging" (Journal of Medical Devices, 2: 501-505, 2008) (5 pages).

Khan et al. "Measurement of laxity in the anterior cruciate ligament-deficient knee: A comparison of three different methods in vitro" (J. Engineering in Medicine, 221; 653-663, 2007).

* cited by examiner 3D knee laxity measurement

METHOD AND SYSTEM FOR MEASURING THE LAXITY OF A JOINT OF A HUMAN OR AN ANIMAL

CROSS REFERENCE TO RELATED APPLICATIONS

This is the § 371 U.S. National Stage of International Application No. PCT/DK2018/050003, filed Jan. 8, 2018, which was published in English under PCT Article 21(2), which in turn claims the benefit of DK Application No. PA 2017 70017, filed Jan. 11, 2017, which is incorporated herein in its entirety.

FIELD OF THE INVENTION

The present invention relates to the determination of the laxity of a joint of a human or an animal, and in particular to such determination which can be performed in a well-defined and reproducible way.

BACKGROUND OF THE INVENTION

The ligaments of a joint play a critical role in stabilizing the joint. The stability of the joint, also referred to as the joint laxity, is therefore an indicator of the functioning of the ligaments. In order to assess the ligaments for injury, plan treatment or follow up after intervention, information about the laxity of the joint is therefore important. Such an evaluation of the laxity of a joint is also relevant e.g. during the process of the implementation of a knee prosthesis or the replacement of ligaments. In practise, this evaluation is often done by a doctor manually applying a force to a part of the body connected to the joint and manually sensing the resulting movement of the joint. However, such a determination is highly dependent on the experience of the person making the assessments.

In order to obtain a less subjective measure of the joint laxity, a number of attempts have been made to develop reproducible methods of determining joint laxity. The simplest existing approach is to measure the displacement of the bones under load by assuming that the visible movements of areas on the skin surface are related to the underlying bone movements. A measuring device adapted for such measurements has been presented in Khan R. T. et. al., J. Engineering in Medicine, 221; 653-663, 2007. However, this kind of method has been shown to not lead to accurate estimates of the laxity as the soft tissue around the joints and bones means that the skin measurements do not correctly reflect the bone movements. Furthermore, it is typically limited to only one and two directions, which is not always sufficient.

Alternatively, the relative movement of the bones connected in a joint can be estimated with MRI scans obtained while loads are applied to the joint. An example of a combined loading device and MRI scanner is presented in Carpenter R. D. et. al., Journal of Medical Devices, 2: 501-505, 2008. However, an MRI scan typically takes several minutes during which period of time the person being investigated must lay completely still. This leads to long measurement periods since one MRI scan must be obtained for each loading that is assessed. Furthermore, this scanning method does not allow metallic parts around the patient which prohibits its use for post-operative assessment following implantation of metal implants.

Yet another approach is to assess the relative position and orientation of the bones by using X-rays. However, it is well-known that the exposure to X-ray radiation should be minimised as it may cause health risks. Therefore, this method is not optimal for a prolonged or repeated assessment. A further challenge with this technique is to avoid undesired interference between a loading device and the X-rays.

Yet another kind of method is to perform bone-fixed measurement in which a part of the measurement device is fixed directly to the bones e.g. by use of pins or screws. Hereby, accurate measurements of the bone movements can be made. However, this approach is invasive and, therefore, not applicable in daily clinical examination. A device based on this principle is disclosed in WO2010/083301. It is designed for intra-operative use only and is intended to be used during total knee replacement surgery.

Hence, an improved method and system for determining the laxity of a joint would be advantageous, and in particular a more efficient and/or reliable method and system would be advantageous.

OBJECT OF THE INVENTION

It is an object of the present invention to provide a method and system for determining the laxity of a joint in a more well-defined and reproducible manner than with known methods and systems.

It is another object of the present invention to provide a method and system for determining the laxity of a joint with which it is possible to get a quantitative measure of the laxity.

It is an object of at least some embodiments of the invention to provide a method and system for determining the laxity of a joint in a more time-efficient manner than with at least some known methods and systems.

It is another object of at least some embodiments of the invention to provide a method and system for determining the laxity of a joint with the joint being exposed to a lower radiation emission than with at least some known methods and systems.

It is a further object of the present invention to provide an alternative to the prior art.

In particular, it may be seen as an object of the present invention to provide a method and system for determining the laxity of a joint that solves the above mentioned problems of the prior art.

SUMMARY OF THE INVENTION

Thus, the above-described object and several other objects are intended to be obtained in a first aspect of the invention by providing a method of determining the laxity of a joint of a human or an animal, the method comprising:
  providing at least one patient-specific geometrical model of at least one bone and/or at least one prosthesis comprised by the joint,
  providing a series of actual images of the joint obtained while known loads were applied to the joint or to a part of the body connected to the joint,
  registering the patient-specific geometrical model onto the actual images,
  based thereon calculate relative displacement and/or rotation of the at least one bone and/or at least one prosthesis as a function of the applied loads, and
  based on the calculated relative displacement and/or rotation determine a measure of the laxity of the joint.

In a second aspect, the invention relates to a system which is adapted to perform the method according to the first aspect; this will be described in further details below.

By "laxity" is preferably meant the slackness, stiffness, or looseness of the joint. It can thus be defined by the amount a joint or ligament deviates from its initial position when a force is applied to it. Laxity can be determined as an absolute measure, such as measured in mm, or a relative measure, such as measured in percent. This means that it is possible to obtain a quantitative measure of the laxity in a well-defined and reproducible way.

The determination of the laxity of a joint is often done in relation to a worn or damaged joint, such as following an accident. It can e.g. be determined in relation to planning and monitoring a recovery process. In that case, "laxity" will typically be defined in comparison to a normally functioning joint. It may e.g. be a movement for a given load in percentage of a similar movement of a normally functioning joint. Thus, such a comparative measure can be referred to as relative. Determination of the laxity of a joint is also done in relation to repair of a joint by inserting a prosthesis. In that case, the laxity may be a measure of the looseness of the joint compared to the joint before the prosthesis was inserted or relative to a normally functioning joint.

A method according to the present invention may in principle be related to any joint in a body of a human or animal patient. It may e.g. be determined for one or more of the following joints: knee, elbow, shoulder, hip, wrist, and ankle. The knee, elbow and ankle each comprises two joints, e.g. the tibiofemoral and the patellofemoral joints for the knee, and the method can be used to determine the laxity of any of these joints.

By "actual images" is preferably meant images obtained at the time of applying the loads. It will typically be digital images which are compared to at least one digital patient-specific geometrical model stored in a memory of a computer or accessible by a computer from an external memory, so that the comparison and the following method steps can be performed by the computer.

In some embodiments of the invention, the method as described provides a series of actual images by the method comprising the steps of:
  applying known loads to the joint or to a part of the body connected to the joint, and
  obtaining a series of actual images of the joint while the loads are applied.

This means that in such embodiments, the steps of applying the loads and obtaining the actual images form part of the invention whereas in the embodiments as previously described, these steps are preferably not included in the invention. On the contrary, the actual images have been previously obtained either shortly before or at any previous point in time, such as several days or weeks before the method of determining the laxity is performed.

In some embodiments of the invention, only one patient-specific geometrical model is used. In other embodiments, more than one patient-specific geometrical model is used. In the latter case, such models may e.g. be models obtained by more than one image-generating technique or models obtained at different times, such as before and after insertion of a prosthesis. The use of more than one model may thus be used to obtain a higher degree of accuracy.

During the application of the known loads, one of the bones of the joint is typically fixated and the relative movement of the one or more other bones of the joint relative thereto is measured. Corresponding measurements can be performed in relation to prostheses. The fixation may e.g. be done by use of straps tightened around a part of the body connected to the joint.

In some embodiments of the invention, the at least one patient-specific geometrical model is obtained from at least one medical image and/or at least one CAD model, such as medical images obtained by a CT scanner or a MRI scanner. The use of CAD models will be relevant in relation to prostheses, as the manufacturing thereof may typically involve such CAD models.

The loads may be applied in multiple spatial directions. Hereby it will be possible to determine a measure of the 3D laxity.

The at least one patient-specific geometrical model may be a 3D model, and the relative displacement and/or rotation may be calculated in 3D so that 3D laxity properties of the joint can be determined.

The actual images may be bi-planar X-ray images, ultrasound images, CT or MRI images.

In presently preferred embodiments of the invention, the loads may be applied by a loading device at least partly arranged inside a bi-planar X-ray scanner so that the joint under assessment is positioned inside the scanner. By "bi-planar" is preferably meant that the images are taken in two planes which may be perpendicular to each other but which could also be at other angles.

The actual images may be obtained by use of a slot scanner. In a slot scanner in the form of an X-ray scanner, the X-ray source and the detector are moved along the joint while a series of images are obtained. Hereby, a larger measurement area can be covered without having to move the person or animal.

In some embodiments comprising the use of a slot scanner, this slot scanner is an EOS® scanner. An EOS® scanner is a bi-planar X-ray scanner, which is characterized as exposing the joint to a lower dose of X-ray radiation than traditional X-rays, such as in the order of 1/10 of the dose of traditional X-rays. It is manufactured and sold by the company EOS Imaging. The EOS system provides low dose, partly or full body, stereo-radiographic images of a patient. The EOS system is designed around a vertically traveling arm supporting two image acquisition systems mounted at right angles. Each acquisition system is composed of an X-ray tube and a linear detector. This bi-planar design and linear, vertical scanning technique acquires frontal and lateral images of a patient simultaneously in either a standing or seated position. By using a lower dose of X-ray radiation, the determination of the laxity involves a lower risk of negative influences to the health of the person or animal being investigated even if the measurements are carried out over a longer period, such as measurements being performed several times.

The registering of the patient-specific geometrical model onto the actual images may be performed by matching features of the actual images against the patient-specific geometrical model. Such a method may e.g. include computations to minimize the least-square difference between bone contours on X-rays and the projections of the contours of the geometrical models on the X-ray image planes. Alternatively, for some embodiments of the invention, the registering may be performed by optimization of the match between X-rays and digitally reconstructed radiographs (DRR) in the original X-ray image planes. A number of numerical methods useful for this purpose exists and will be well-known to a person skilled in the art.

In a second aspect, the present invention relates to a system for determining the laxity of a joint of a human or animal, the system comprising:

means for providing at least one patient-specific geometrical model of at least one bone and/or at least one prosthesis comprised by the joint, loading device for applying known loads to the joint or to a part of the body connected to the joint, image forming device for obtaining a series of actual images of the joint while the loads are applied, and at least one computer adapted to:
register the at least one patient-specific geometrical model onto the actual images,
based thereon calculate relative displacement and/or rotation of the at least one bone and/or at least one prosthesis as a function of the applied loads, and
based on the calculated relative displacement and/or rotation, determine a measure of the laxity of the joint.

In such a system, the means for providing at least one patient-specific geometrical model may be adapted to base the at least one patient-specific geometrical model on medical images obtained by a CT scanner or a MRI scanner and/or CAD models. The loading device may be adapted to apply the loads in multiple spatial directions. The loading device may be shaped and dimensioned so that it is adapted to be arranged inside a slot scanner as will be explained in further details in relation to the figures.

"Means for providing at least one patient-specific geometrical model" may be a computer forming part of the system, but it may also be a connection, such as a cable or an internet-connection, for retrieving the model from another computer or storage medium not forming part of the system.

In some embodiments of the invention, the image-forming device is an X-ray apparatus or an ultrasound apparatus. The image-forming device may be a slot scanner, such as an EOS® scanner.

The computer of the system may be adapted to perform the registration of the patient-specific geometrical model onto the actual images e.g. by an iterative closest point optimization or, for some embodiments of the invention, the optimization of the match between the X-rays and digitally reconstructed radiographs (DRR) in the original X-ray image planes.

In a third aspect, the invention relates to a computer readable medium having instructions stored thereon, wherein the instructions, when executed by a processor, cause the processor to perform the method as described above, comprising:

retrieving from a first storage medium at least one patient-specific geometrical model of at least one bone and/or at least one prosthesis comprised by the joint, retrieving from the first storage medium or from a second storage medium a series of actual images of the joint obtained while known loads were applied to the joint or to a part of the body connected to the joint, registering the at least one patient-specific geometrical model onto the actual images, based thereon calculate relative displacement and/or rotation of the at least one bone and/or at least one prosthesis as a function of the applied loads, and based on the calculated relative displacement and/or rotation determine a measure of the laxity of the joint.

The first, second and third aspects of the present invention may each be combined with any of the other aspects of the invention. E.g., the computer readable medium according to the third aspect may be adapted to perform any of the steps as described for the method according to the first aspect.

These and other aspects of the invention will be apparent from and elucidated with reference to the embodiments described hereinafter.

BRIEF DESCRIPTION OF THE FIGURES

The method and system for determining the laxity of a joint of a human or an animal according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
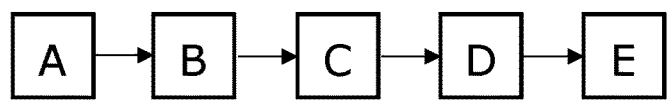
FIG. 1 is a flow-chart of a method according to the invention.

FIG. 1 schematically shows a flow-chart of the method of determining the laxity of a joint of a human or an animal according to the present invention; more details of the method steps will be given in the following figures. The method comprises the following steps which will be described in details below:

(A) providing at least one patient-specific geometrical model of at least one bone and/or at least one prosthesis comprised by the joint, (B) providing a series of actual images of the joint obtained while known loads were applied to the joint or to a part of the body connected to the joint, (C) registering the at least one patient-specific geometrical model onto the actual images, (D) based thereon calculate relative displacement and/or rotation of the at least one bone and/or at least one prosthesis as a function of the applied loads, and (E) based on the calculated relative displacement and/or rotation determine a measure of the laxity of the joint.

The steps shown in FIG. 1 will each correspond to a part of a system according to an aspect of the invention.

Figure 2:
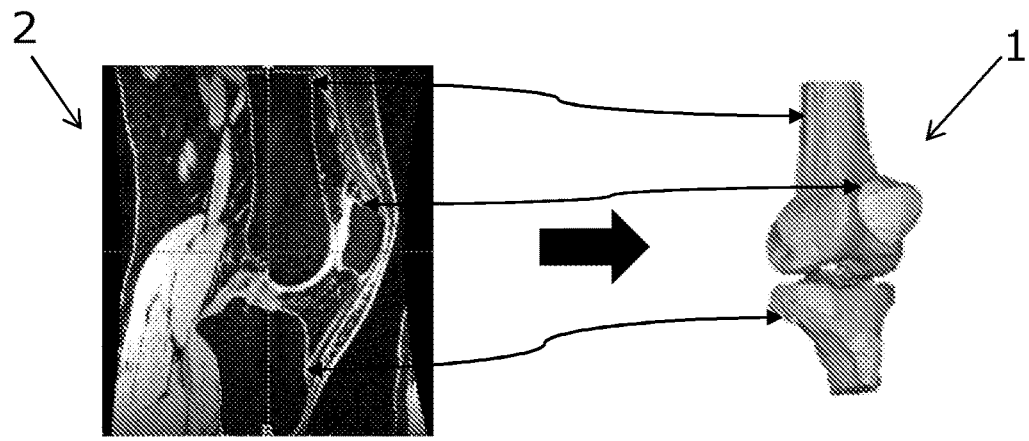
FIG. 2 shows an example of a constructed 3D model of a bone based on a MRI image.
Figure 3:
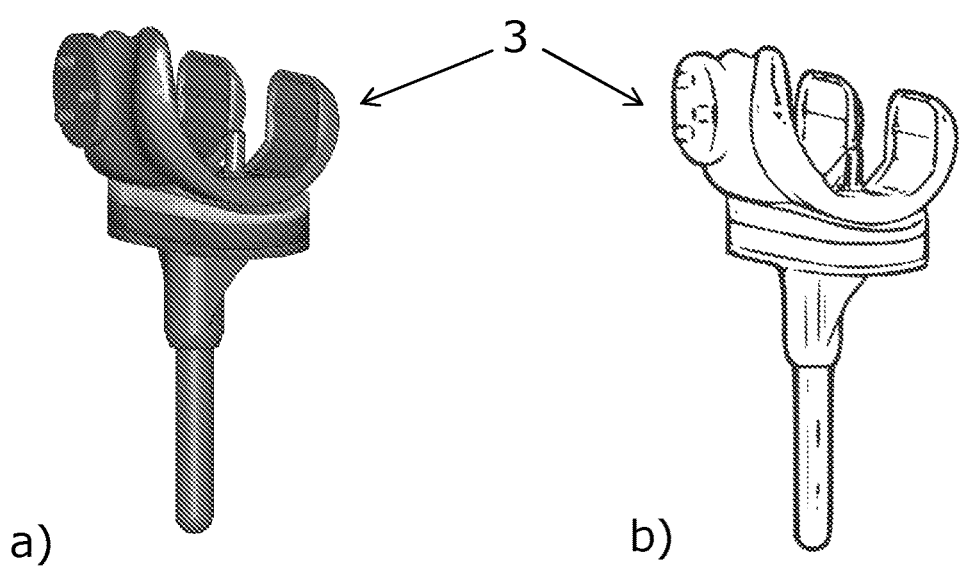
FIG. 3 shows an example of a 3D model of a prosthesis; two different representations of the same model are shown in FIGS. 3.a and 3.b.

The at least one patient-specific geometrical model may e.g. be obtained from at least one medical image and/or at least one CAD model. FIG. 2 shows an example of how a 3D-model 1 can be constructed from digital images 2 (only one shown in the figure) obtained by a MRI scanner. The arrows in the figure schematically show which part of the contours in the digital image that matches the resulting bone contour in the model. FIG. 3 shows an example of a 3D model 3 of a prosthesis. FIG. 3.a shows the model as solid, and FIG. 3.b shows the same model as line drawing. The two different representations are given to show the features of the model as comprehensively as possible.

Figure 4:
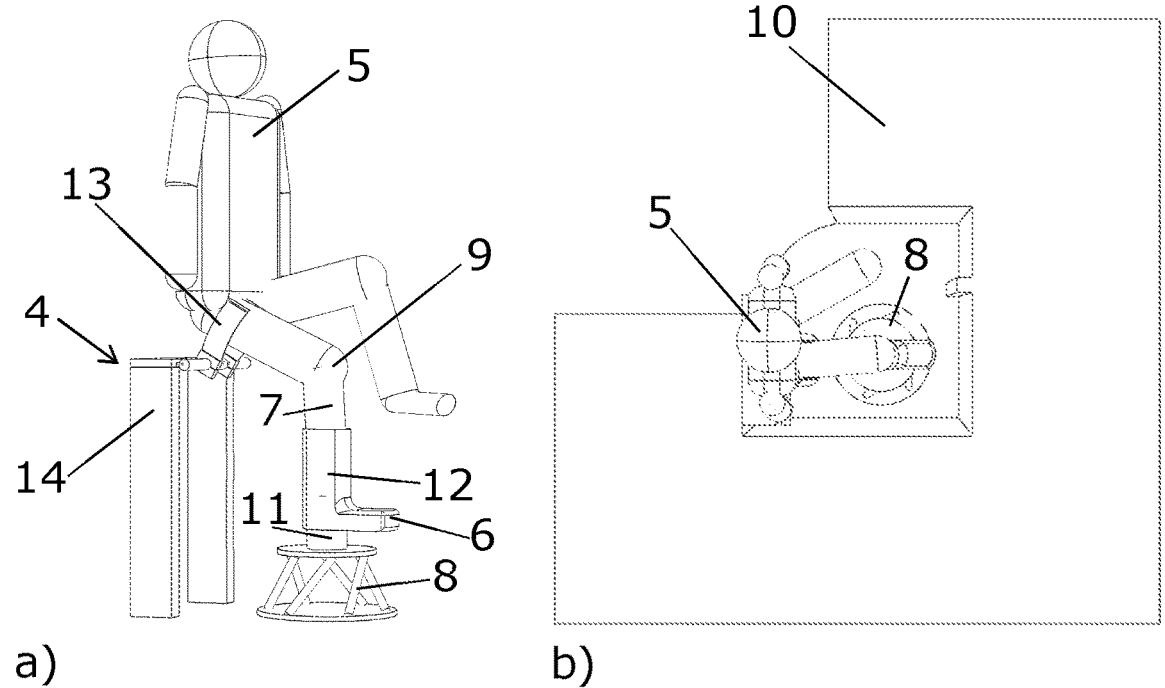
FIG. 4 schematically shows an example of a loading device where the loads can applied in multiple spatial directions.
Figure 5:
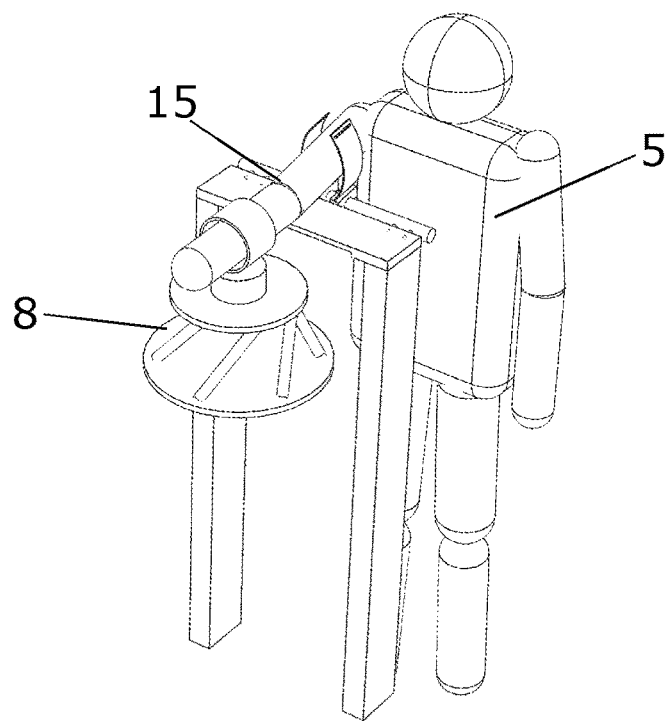
FIG. 5 schematically shows how loads can be applied to an elbow.

FIG. 4 schematically shows a possible embodiment of a loading device 4 which can be used to apply the loads. However, any way of applying known loads in a controlled manner is covered by the scope of the present invention. With such an embodiment, the loads can be applied in multiple spatial directions. FIG. 4.a shows a side view of a person 5 having the right foot 6 and the lower part of the shank 7 fastened to a parallel manipulator 8; such a parallel manipulator 8 is known on its own, and the use and control thereof will be well known to a person skilled in the art. It can be used to provide both translational and rotational movement of the shank 7 resulting in corresponding forces being applied to the knee 9. FIG. 4.b shows a top view of the loading device in FIG. 4.a arranged inside a slot scanner 10. The loading device 4 comprises a six degrees of freedom parallel manipulator 8 and a six-axis force and moment sensor 11. It further comprises a shank fixation component 12, a thigh fixation component 13, and an adjustable seat 14. The illustrated loading device 4 is controlled by a computer (not shown). The loading device 4 can also be used for applying load to the elbow 15; an example of such an embodiment is shown schematically in FIG. 5.

Figure 6:
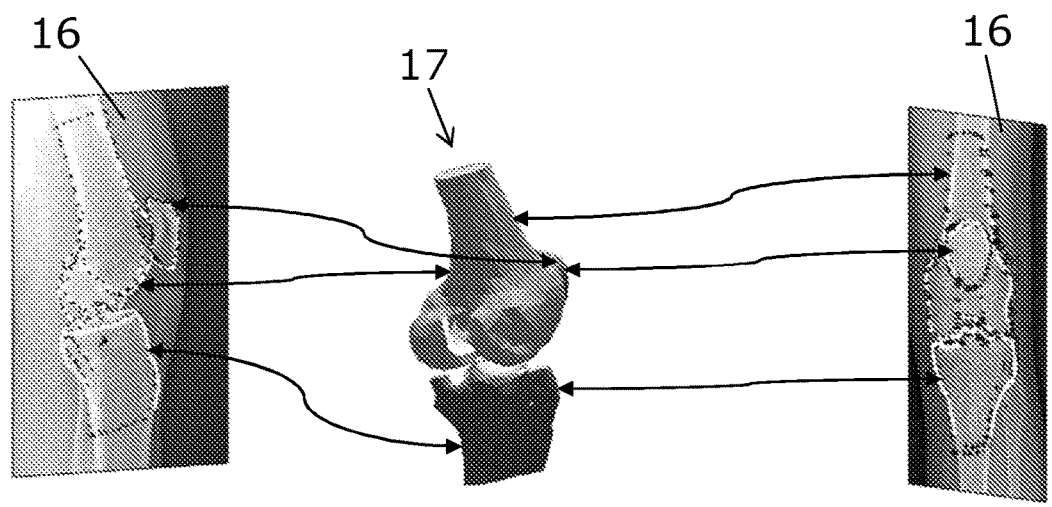
FIG. 6 schematically shows how 3D positions and orientations of 3D geometrical models of femur, patella and tibia can be reconstructed from the frontal and lateral X-ray images obtained as shown in FIG. 4.

FIG. 6 is an illustration of how to obtain the 3D positions and orientations of 3D geometrical models of femur, patella and tibia reconstructed from the actual images 16, i.e. the frontal and lateral X-ray images 16 obtained as shown in FIG. 4.b. The arrows in the figure schematically show which parts of the contours in the actual image 16 that match the resulting bone contour 17. The reconstruction has been accomplished by minimizing the difference in the measured X-ray contour and the contour of the models projected onto the X-ray images; this is an example of a method including an iterative closest point optimization. By using a patient-specific geometrical model which is a 3D model, and calculating the relative displacement and/or rotation in 3D, it is obtained that 3D laxity properties of the joint can be determined.

Figure 7:
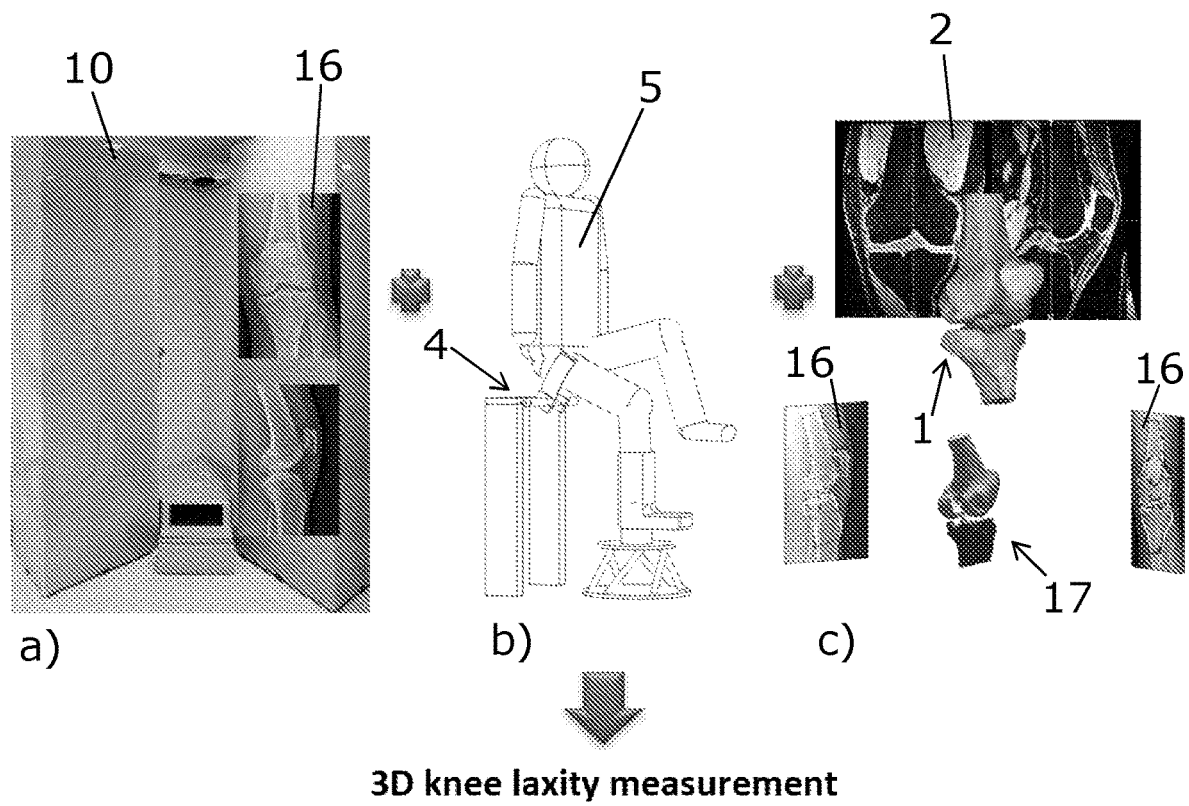
FIG. 7 schematically summarizes an example of the method according to the invention.

FIG. 7 schematically summarizes an example of the method as described above. FIG. 7.a schematically shows a slot scanner 10, such as an EOS® scanner, by use of which the actual images 16 are obtained. FIG. 7.b schematically shows the loading device 4, and FIG. 7.c schematically shows bone pose reconstruction. The invention can thus be seen as a combination of several techniques, which are not normally combined. In the example in FIG. 7, the 3D laxity of a joint is thus obtained from a combination of a slot scanner 10, a loading device 4 and 3D bone models 1. The calculation of a measure of the laxity based on displacements and rotations will typically be based on tables or equations describing such known relationships. Which specific kind of relationships to use may be determined as part of a design process for a given system, and it may also include use of neural networks to continuously build new information into the system.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. In addition, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A system for determining a laxity of a joint of a human or animal, the system comprising:
   a means for providing at least one patient-specific geometrical three-dimensional (3D) model of at least one bone and/or at least one prosthesis comprised by the joint,
   a loading device configured to move an object with six independent degrees of freedom (DOE) for applying known loads including at least two known loads having different selected vectors to the joint or to a part of the body connected to the joint, the loading device configured to apply the known loads in multiple spatial directions,
   an image forming device for obtaining a series of actual images of the joint while the loads are applied, the image forming device configured to acquire 3D image information that comprises the actual images, and
   at least one computer adapted to:
      register the at least one patient-specific geometrical model onto the actual images,
      calculate a relative displacement and rotation of the at least one bone and/or at least one prosthesis as a function of the applied known loads including the at least two known loads having different selected vectors, the relative displacement and rotation based on registering the patient-specific geometrical 3D model onto the actual images, and
      determine a measure of the laxity of the joint based on the calculated relative displacement and rotation, wherein the relative displacement and rotation is calculated in 3D so that 3D laxity properties of the joint can be determined.

2. The system according to claim 1, wherein the means for providing at least one patient-specific geometrical model is adapted to base the at least one patient-specific geometrical model on medical images obtained by a CT scanner or a MRI scanner and/or CAD models.

3. The system according to claim 1, wherein the image-forming device is an X-ray apparatus or an ultrasound apparatus.

4. The system according to claim 3, wherein the image-forming device is a slot scanner.

5. The system according to claim 1, wherein the computer is adapted to perform the registering of the patient-specific geometrical model onto the actual images by an iterative closest point optimization or a match between digitally reconstructed radiographs and the actual images.

6. The system according to claim 1, wherein the loading device comprises a six-axis force and moment sensor.

7. The system according to claim 1, wherein the loading device comprises a shank fixation component, a thigh fixation component, and an adjustable seat.

8. The system according to claim 1, wherein the loading device is at least partially arranged within the image forming device.

9. The system according to claim 1, wherein the loading device comprises a six degrees of freedom parallel manipulator.

10. A method of determining the laxity of a joint of a human or an animal using the system of claim 1, the method comprising:

providing at least one patient-specific geometrical three-dimensional (3D) model of at least one bone and/or at least one prosthesis comprised by the joint, providing a series of actual images of the joint obtained while known loads including the at least two known loads having different selected vectors were applied to the joint or to a part of the body connected to the joint, the known loads being applied in multiple spatial directions, registering the at least one patient-specific geometrical 3D model onto the actual images, calculating a relative displacement and rotation of the at least one bone and/or at least one prosthesis as a function of the applied known loads including the at least two known loads having different selected vectors based on registering the patient-specific geometrical 3D model onto the actual images, wherein the relative displacement and rotation is calculated in 3D so that 3D laxity properties of the joint can be determined, and based on the calculated relative displacement and rotation determine a measure of the laxity of the joint including 3D laxity.

11. The method according to claim 10, wherein the at least one patient-specific geometrical model is obtained from at least one medical image and/or at least one computer-aided design (CAD) model, such as medical images obtained by a computed tomography (CT) scanner or a magnetic resonance imaging (MRI) scanner.

12. The method according to claim 10, wherein the actual images are bi-planar X-ray images, ultrasound images, CT or MRI images.

13. The method according to claim 10, wherein the known loads are applied by the loading device and the loading device is at least partly arranged inside the image forming device, which comprises a bi-planar X-ray scanner so that the joint is positioned inside the scanner.

14. The method according to claim 10, wherein the actual images are obtained by use of a slot scanner.

15. The method according to claim 10, wherein the registering of the patient-specific geometrical model onto the actual images is performed by an iterative closest point optimization or a match between digitally reconstructed radiographs and the actual images.

16. A computer readable medium having instructions stored thereon, wherein the instructions, when executed by a processor, cause the processor to perform the method of claim 10, further comprising:

retrieving from a first storage medium at least one patient-specific geometrical model of at least one bone and/or at least one prosthesis comprised by the joint, retrieving from the first storage medium or from a second storage medium a series of actual images of the joint, two or more of which were obtained while the known loads of different selected vectors were applied to the joint or to a part of the body connected to the joint, registering the at least one patient-specific geometrical model onto the actual images, calculating relative displacement and rotation of the at least one bone and/or at least one prosthesis as a function of the applied known loads including the at least two known loads having different selected vectors, the relative displacement and rotation based on registering the patient-specific geometrical 3D model onto the actual images, and determining a measure of the 3D laxity of the joint based on the calculated relative displacement and rotation.

* * * * *